United States Patent [19]

Egly et al.

[11] 4,394,220

[45] Jul. 19, 1983

[54] PROCESS FOR RECTIFICATION OF PROPANE NITRATION STREAM

[75] Inventors: Richard S. Egly, West Terre Haute; Cecil E. Turnquist, Terre Haute, both of Ind.

[73] Assignee: Angus Chemical Company, Northbrook, Ill.

[21] Appl. No.: 313,862

[22] Filed: Oct. 22, 1981

Related U.S. Application Data

[63] Continuation of Ser. No. 182,921, Sep. 2, 1980, abandoned.

[51] Int. Cl.³ .......................... B01D 3/34; B01D 15/00
[52] U.S. Cl. ........................................ 203/42; 203/97; 203/98; 568/947

[58] Field of Search .................. 568/947, 948; 203/95, 203/96, 97, 98, 39, 40, 42

[56] References Cited

U.S. PATENT DOCUMENTS 2,117,931  5/1938  Allen ................................. 568/948
3,480,517  11/1969  Tindall et al. ...................... 568/948

Primary Examiner—Frank Sever
Attorney, Agent, or Firm—Leydig, Voit, Osann, Mayer & Holt, Ltd.

[57] ABSTRACT

It is the discovery of the present invention to provide an improved method of rectifying the crude production stream obtained by the vapor phase nitration of hydrocarbons by subjecting the absorber bottom mixture to extractive distillation with water.

3 Claims, 1 Drawing Figure

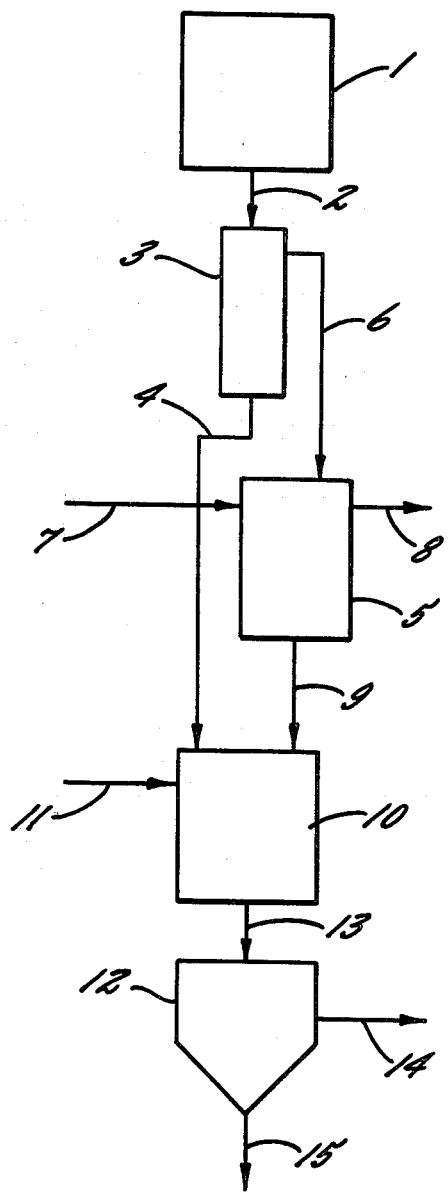

PROCESS FOR RECTIFICATION OF PROPANE NITRATION STREAM

This is a continuation of copending application Ser. No. 182,921, filed Sept. 2, 1980, now abandoned.

BACKGROUND OF THE INVENTION

This invention relates to a method of rectifying a reaction product stream. In a particular aspect, this invention relates to a process for rectifying the crude production stream obtained by the vapor phase nitration of hydrocarbons.

Hass, Hodge and Vanderbilt, U.S. Pat. No. 1,967,667, disclosed a process for the production of nitroalkanes by the vapor phase nitration of hydrocarbons, e.g. propane, at elevated temperatures and pressures. The nitration reaction with propane produces the four lower nitroalkanes and numerous by-products which are difficult to separate.

According to the present process, the vapor phase nitration stream from the nitration chamber (i.e., the nitrator) is passed through a condenser which condenses most of the normally-liquid components and separates them from normally-gaseous ones, including unreacted propane. The gaseous portion passes into a water absorber where the gas is washed of water soluble components, thereby forming the absorber bottoms. These absorber bottoms contain nitroalkanes, acetaldehyde, and other oxygenated products, etc., but only a small proportion of the normally gaseous components such as propane, CO2, CO, nitrogen and nitrogen oxides. The liquid from the condenser and the absorber bottoms are then stripped by distillation of nitroalkanes, low boiling compounds and compounds of low water solubility. The recovered condensate forms a water and an oil layer, the latter consisting largely of crude nitroalkanes plus low boiling components. This mixture of crude nitroalkanes is then delivered to a heads column where the low boilers are stripped and the remaining nitroalkanes, containing 0.05 to 0.5% formaldehyde, are then fractionated to give commercial grade nitromethane, nitroethane, 1-nitropropane and 2-nitropropane.

This process has served well for many years, but severe fouling of the heads column and reboiler by a carbonaceous material of unknown origin causes considerable difficulty. Accordingly, there is a need for an improved rectification process.

SUMMARY OF THE INVENTION

It is an object of this invention to provide a method of rectifying a reaction product stream.

It is another object of this invention to provide an improved process for rectifying the crude production stream obtained by the vapor phase nitration of hydrocarbons.

Other objects of this invention will be apparent to those skilled in the art from the description herein.

It is the discovery of the present invention to provide an improved method of rectifying the crude production stream obtained by the vapor phase nitration of hydrocarbons by subjecting the condensed product and the absorber bottom mixture to the step of extractive distillation with water.

DETAILED DISCUSSION

With reference to the drawing, an alkane, e.g. propane, is nitrated in nitrator 1. The reaction mixture is conducted to condenser 3 by line 2 where liquids are condensed and are then delivered to the stripper 10 by line 4. The gases from the condenser are conducted by line 6 to the absorber where gases are washed with water from line 7. The liquid phase from the absorber comprises principally a dilute solution of nitroalkanes and oxygenated products in water, though there may be a small amount of "oil" or primarily organic phase. The gas phase exits from the absorber through line 8 and the liquid phase, the absorber bottoms, is conducted through line 9 to the stripper 10, where it and liquids from the condenser are subjected to extractive distillation with water from line 11. The distillate is collected in decanter 12 through line 13 where it forms two layers, a water layer and a nitroalkane layer. The heavier water layer is discharged through line 15 and the nitroalkane layer is drawn off through line 14.

The improved processing step of this invention is the countercurrent extractive distillation step carried out at 11. By use of the extraction step, the formaldehyde content of the distillate can be reduced by as much as 90% and the $NO_x$ (mixed nitrogen oxides) content as much as 80%. The resulting advantages include virtual elimination of the build-up of carbonaceous material in the heads column and reboiler and improved stability of the nitroalkanes.

It is understood that the improvement step is not limited to the crude nitration product obtained by the nitration of propane. Rather, it is intended that the improvement step can be used equally well with the nitration stream from the nitration of methane, ethane, or butane.

In carrying out the improvement step of this invention, it has been found that formaldehyde removal increases proportionately to the ratio of extraction water volume to vaporized nitroalkanes. For example, about 90% of the formaldehyde content can be removed at a liquid (water) to vapor (nitroalkane) ratio of about 1.0 for 10 extraction trays or about 2.5 for 5 extraction trays. The extraction step is carried out at the top of the distillation column by passing water, preferably distilled water, countercurrently through the nitroalkane vapors.

The invention will be better understood with reference to the following examples. It is understood, however, that the examples are intended only to illustrate the invention and it is not intended that the invention be limited thereby.

EXAMPLE 1

An Oldershaw fractionation column consisting of three perforated plate sections was adapted to provide 30 trays for stripping and 10 trays for extraction. The column contained plates that were one inch in diameter and 80 perforated holes 0.035 inch in diameter per plate. The bottom section, consisting of 20 trays, and the middle section consisting of 10 trays were used for stripping. The remaining 10 trays were used for extraction. The column was provided with vacuum jackets, silvered on the inside, to minimize heat loss. A two-liter distillation flask equipped with a glass mantle heating source and temperature controls was attached to the bottom of the column. A water-cooled Allihn, bulb-type condenser and a glycol-cooled Friedricks condenser operated at about −12° C. were connected to the top of the column to cool and condense vapors coming from the column. A cold trap placed inside a Dewar flask in a methanol-dry ice bath was provided to recover a portion of the residual non-condensed vapor. A decanter attached to the condenser was provided to collect condensed vapors, which separated into two liquid layers, the upper being nitroalkanes and the lower being water. Nitroalkanes collected in the decanter overflowed into a graduate cylinder and the water phase was returned as reflux to the top of the stripping section. The distilling flask was fitted with a means for drawing off aqueous solution to provide for continuous bottoms discharge.

A large sample of absorber bottoms and condenser condensate was withdrawn from a commercial unit. It formed two layers which were separated, filtered through cloth and pumped to the extraction column in a ratio of 20 parts of water layer to one part of nitroalkane. This is the approximate ratio in which they are fed to the commercial stripper in the prior process. Water was charged initially to the distillation flask and heated to boiling to provide vapor for stripping. Distilled water was fed continuously to the top of the extraction section. The aqueous bottoms were continuously discharged from the bottom flask of the extraction section through a cooler to a bottoms receiver.

Date for the experimental runs, of which there were six, are given in Table 1 along with data for six non-extractive runs.

TABLE 1

|  | Non-Extractive | Extractive |
|---|---|---|
| Water Phase Feed Rate, ml/min | 15 | 10.0–15.5(12.4)* |
| Oil Phase Feed Rate, ml/min | 0.5–0.91 | 0.40–0.84(0.64) |
| Oil Phase Distillation Rate, ml/min | 1.0–1.55 | 0.51–1.25(0.94) |
| Water Phase Reflux Rate, ml/min | 0.5–1.6 | 0.2–1.05(0.63) |
| Water Extraction Rate, ml/min | — | 0.7–4.2(2.24) |
| Bottoms Rate, ml/min | 14.5–15.0 | 12–16(14.5) |
| Temperatures, °C. | | |
| Bottom Flask | 103–104 | 103–104 |
| Tray 20 | 100–101 | 90–101 |
| Tray 30 | 90–96 | 86–97 |
| Tray 40 | 85–94 | 85–96 |
| Oil Distillate Assay, Wt % | | |
| $NO_x$ | 0.07–0.23(0.145)* | 0.02–0.13(0.1) |
| HCHO | 0.30–0.50(0.39) | 0.03–0.20(0.09) |

*Average

The nitroalkane portions fom these two sets of runs were tested for stability at elevated temperatures. The non-extracted nitroalkane developed more color and solids at a faster rate than the extracted material. Also analyses showed that the rate of change in compositions indicated that the extracted material was more stable than unextracted material.

EXAMPLE 2

The experiment of Example 1 was repeated in all essential details except that the column was modified so that the bottom portion of the column contained 10 trays instead of 20 and the extraction section contained 5 trays instead of 10 and four runs were made. The results are given in Table 2.

TABLE 2

|  | Non-Extractive | Extractive |
|---|---|---|
| Water Phase Feed Rate, ml/min | 15.5 (2 runs) | 14.5 (2 runs) |
|  | 13 (2 runs) | 13 (2 runs) |
| Oil Phase Feed Rate, ml/min | 0.75 (2 runs) | 0.75 (2 runs) |
|  | 0.65 (2 runs) | 0.65 (2 runs) |
| Oil Phase Distillation Rate, ml/min | 1.17–1.40 | 1.18–1.48 |
| Water Phase Reflux Rate, ml/min | 0.72–1.35 | 0.5–1.1 |
| Water Phase Extraction Rate, ml/min | — | 1.8–4.3 |
| Bottoms Rate, ml/min | 12.5–15 | 15.5–17.2 |
| Temperatures, °C. | 103–104 | 103.5–105 |
| Bottom Flask | | |
| Tray 10 | 99–100 | 92–100 |
| Tray 20 | 95–97.5 | 89–98 |
| Tray 25 | 91–95 | 89–95 |
| Oil Distillate Assay | | |
| $NO_x$ | 0.12–0.49(0.30)* | 0.05–0.07 |
| HCHO | 0.26–0.40(0.32) | 0.03–0.18(.09)* |

*Average of all runs

We claim:

1. In a method for rectifying the crude production stream obtained from the process of vapor phase nitration of hydrocarbon to produce nitroalkanes, which includes passing the vapor phase nitration stream from a nitration chamber through a condenser to condense a substantial portion of the normally-liquid components and separate said normally-liquid components from normally-gaseous components, forming absorber bottoms by passing the gaseous components into a water absorber to wash the gas, said absorber bottoms including nitroalkanes, acetaldehyde, nitrogen, nitrogen oxides and oxygenated compounds, stripping the condenser liquid and absorber bottoms by distillation to form a condensate including a water layer and an oil layer, said oil layer comprising crude nitroalkanes and low boiling components, stripping the low boiling components from the condensate in a heads column, and fractionating the oil layer to produce fractions of nitroalkane components, the improvement comprising, subjecting the condenser liquid and absorber bottoms solely to extractive distillation with substantially pure water to remove sufficient impurities therefrom so that the condensate is relatively free of impurities, thereby avoiding carbonaceous build-up in the heads column and fractionater during extraction of the nitroalkanes.

2. The method of claim 1 wherein the water used for extraction is used in a volume of about 1 part of liquid to one part of nitroalkane vapors.

3. The method of claim 1 wherein the water used for extraction is used in a volume of about 2.5 parts of liquid to one part of nitroalkane vapors.

* * * * *

UNITED STATES PATENT AND TRADEMARK OFFICE
CERTIFICATE OF CORRECTION

PATENT NO. : 4,394,220

DATED : July 19, 1983

INVENTOR(S) : Egly et al.

It is certified that error appears in the above-identified patent and that said Letters Patent is hereby corrected as shown below:

Cover page, category 73, change "Angus" to --ANGUS--.

Signed and Sealed this

First Day of May 1984

[SEAL]

Attest:

Attesting Officer

GERALD J. MOSSINGHOFF

Commissioner of Patents and Trademarks